United States Patent
Bouvier et al.

(10) Patent No.: US 9,974,502 B2
(45) Date of Patent: *May 22, 2018

(54) MOBILE BASE AND X-RAY MACHINE MOUNTED ON SUCH A MOBILE BASE

(71) Applicant: General Electric Company, Schenectady, NY (US)

(72) Inventors: Bernard Bouvier, Eragny sur Oise (FR); Carlos Martinez Ferreira, Paris (FR); Bruno Galloni, Saint Lubin des Joncherets (FR); Jean-Luc Thomé, Saint Grégoire (FR); Guy Jean Sébastien Caverot, Nantes (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/376,295

(22) Filed: Dec. 12, 2016

(65) Prior Publication Data

US 2017/0086764 A1    Mar. 30, 2017

Related U.S. Application Data

(63) Continuation of application No. 14/867,256, filed on Sep. 28, 2015, now Pat. No. 9,545,235, which is a
(Continued)

(30) Foreign Application Priority Data

Dec. 1, 2009    (FR) ...................................... 09 58556

(51) Int. Cl.
| | |
|---|---|
| *A61B 6/03* | (2006.01) |
| *A61B 6/00* | (2006.01) |
| *A61B 6/10* | (2006.01) |

(52) U.S. Cl.
CPC ............ *A61B 6/4405* (2013.01); *A61B 6/102* (2013.01); *A61B 6/4441* (2013.01); *A61B 6/547* (2013.01); *A61B 6/548* (2013.01); *A61B 6/4423* (2013.01)

(58) Field of Classification Search
CPC ....... A61B 6/032; A61B 6/035; A61B 6/4028; A61B 6/4229; A61B 6/4435;
(Continued)

(56) References Cited

U.S. PATENT DOCUMENTS

| | | | |
|---|---|---|---|
| 3,912,037 A | 10/1975 | Krieg | |
| 4,729,660 A * | 3/1988 | Tsumura | ................ G01S 17/06 180/169 |

(Continued)

FOREIGN PATENT DOCUMENTS

JP          5345068 B2    12/1978

*Primary Examiner* — David E Smith

(57) ABSTRACT

A mobile base designed to receive an X-ray machine is provided. An X-ray machine capable of being mounted on the mobile base is also provided. The X-ray machine of the invention is configured to move using a motor-driven system associated with a navigation system. The navigation system of the invention enables the X-ray machine to be moved automatically and with precision from one position to another within an examination, hybrid or operation room. The X-ray machine is also configured for the automatic positioning of the moving parts around the patient, while at the same time keeping the region to be subjected to radiography within an X-ray beam.

20 Claims, 8 Drawing Sheets

Related U.S. Application Data continuation of application No. 13/513,315, filed as application No. PCT/IB2010/003012 on Nov. 4, 2010, now Pat. No. 9,173,628.

(58) Field of Classification Search
CPC ..... A61B 6/4441; A61B 6/4405; A61B 6/547; A61B 6/548; G01D 1/0212; G01D 1/0214; G01D 1/0221; G01D 1/0223; G01D 1/0236

See application file for complete search history.

(56) References Cited

U.S. PATENT DOCUMENTS

| | | | |
|---|---|---|---|
| 4,796,198 A | | 1/1989 | Boultinghouse et al. |
| 4,811,228 A | * | 3/1989 | Hyyppa ............... G01S 5/08 180/169 |
| 6,249,743 B1 | * | 6/2001 | Ohshimo ............ G01C 15/002 342/357.75 |
| 6,814,490 B1 | * | 11/2004 | Suhm ................... A61B 6/4405 378/195 |
| 9,173,628 B2 | * | 11/2015 | Bouvier ............... A61B 6/4405 |
| 9,545,235 B2 | * | 1/2017 | Bouvier ............... A61B 6/4405 |
| 2008/0161672 A1 | * | 7/2008 | Marar .................. A61B 5/055 600/407 |
| 2008/0192895 A1 | * | 8/2008 | Dehler ................. A61B 6/4405 378/94 |

* cited by examiner

MOBILE BASE AND X-RAY MACHINE MOUNTED ON SUCH A MOBILE BASE

CROSS REFERENCE TO RELATED APPLICATIONS

This application is a continuation of U.S. application Ser. No. 14/867,256, filed Sep. 28, 2015, which is a continuation of U.S. application Ser. No. 13/513,315 filed Jun. 1, 2012, now U.S. Pat. No. 9,173,628, which is a filing under 35 U.S.C. § 371(c) and claims priority to international patent application number PCT/IB2010/003012, filed on Nov. 4, 2010, published on Jun. 9, 2011, as WO 2011/067648, which claims priority to French Patent Application Serial No. 0958556, filed Dec. 1, 2009, now French Patent No. 2953119, all of which are incorporated herein by reference in their respective entireties.

BACKGROUND OF THE INVENTION

Field of the Invention

Embodiments of the subject matter disclosed herein generally relate to a mobile base designed to receive an X-ray machine. An object of embodiments of the present invention is also an X-ray machine that can be mounted on said mobile base. Embodiments of the present invention find application in medical imaging, and more particularly in the field of medical diagnostic apparatuses.

The X-ray machine of the invention is designed especially for a hospital ward, such as a surgical ward, an anesthetic room, a diagnostic unit, an intensive care unit or a ward known as a hybrid ward used to meet the requirements of both angiography rooms and operation rooms.

Description of the Related Art

In the prior art, X-ray diagnostic machines are X-ray image acquisition machines. These machines are used to obtain images or even sequences of images of an organ situated inside a living being, especially a human being.

In the prior art, X-ray machines have moving parts that enable them to rotate about the patient in different directions. These moving parts are capable of moving in all three dimensions of a space. These moving parts generally consist of an arm having an X-ray tube at one of its ends and a detector at the other one of its ends. This tube sends out an X-ray beam along a direction of emission.

These X-ray machines are used for angiography examinations for diagnostic or interventional purposes.

During these examinations, it is necessary to take X-ray exposures of the region undergoing diagnosis or intervention. To this end, the patient is positioned between the X-ray tube and the detector and more specifically he or she is placed that the region to be X-rayed is in a facing position.

There presently exist several types of X-ray machines used to carry out the radiography exposures, for example X-ray machines fixed to the ground in an examination room. These X-ray machines have several degrees of freedom by which the X-ray beam can be positioned before the region of interest. However, this type of X-ray machine is not suited to an operating ward. Indeed, for certain examinations, X-rays are needed only at the beginning and at the end of the operation. In between these two points, the emphasis is on access to the patient. Since these angiography machines are fixed to the ground, they cannot be moved away from the patient support table or bed at a time when the presence of the radiography system is not necessary. Furthermore, the stages of placing and moving the patient on the table become more difficult because this bulky system cannot be moved away.

There also exist X-ray machines called "mobile surgical units" that can be moved manually. These machines generally have a large trolley supporting a large number of batteries used to power the X-ray tube. However, this type of X-ray machine has drawbacks. Indeed, these machines are not suited to angiography procedures. For the necessary power delivered by the X-ray tube is not sufficient to perform the angiography procedures which require excellent image quality.

Furthermore, these mobile X-ray machines do not provide for complex angular movements because the diameter of the arm that supports the tube and the detector is not big enough. Similarly, these mobile X-ray machines do not reach sufficient rotation speeds to enable high quality 3D image reconstruction like those needed in a present-day angiography machine. These mobile X-ray machines are also not suited to angiography procedures requiring certain automated motions needed for certain applications, especially 3D reconstruction.

Furthermore, even if the weight of such a machine is half that of an X-ray machine intended for angiography, it is still very difficult to move because of its large size and its weight (about 300 kg).

There are also X-ray machines for angiography that are suspended from the ceiling and can be moved on rails all along the ceiling, through a mobile trolley and by means of an electrical motor. However, this type of X-ray machine has drawbacks. Indeed, an operation room generally has a patient's support table, lighting means, systems to distribute medical fluids, supports for anesthetic equipment, supports for electrical scalpels and supports for perfusion pumps. Most of these systems are fixed to the ceiling around the patient's table depending on the constraints of an operations room, thus cluttering the space around the patient's table. Consequently, owing to the space requirement of the rails fixed to the ceiling and the volume of the X-ray machine, their installation in a surgical ward as an angiography machine is quite impossible.

Furthermore, the fact of mounting an X-ray machine on the ceiling considerably increases the risk of opportunistic infection in the patient. Indeed, these X-ray machines suspended on the ceiling are designed to be positioned above the patient or in his immediate vicinity and therefore in the immediate vicinity of the operating site thus increasing the risk of particles falling from the machine.

Furthermore, this fact of suspending the X-ray machine or machine gives rise to difficulties in cleaning and maintaining this machine properly. Thus, it becomes impossible to mount this type of X-ray machine adapted to environments of varying sterility. Indeed, operating rooms are constantly sterilized and the fact of having rails on which the X-ray machine slides above the patient increases the risks of nosocomial illness or septicemia owing to the difficulty of cleaning these apparatuses Furthermore, in certain surgical wards, a sterile laminar flow is set up above the patient. In this case, the rails enable the machine to be made to slide on the ceiling with the laminar flow, and this has the effect of blowing particles present on the into the sterile zone.

There also exist X-ray machines for angiography based on the technology of industrial robots generally found in automobile plants. However, X-ray machines of this type have drawbacks. Indeed, the arms fitted to these robots generally have a relatively substantial space requirement for the space available in as surgical ward. Consequently, the movement of these arms creates risks of safety for people working in a surgical ward. Consequently, the installation of these robots as angiography machines in a surgical ward is quite impossible.

The need has become felt for some time now for an X-ray machine suited to what are called hybrid rooms, making it possible: firstly to meet the needs of angiography, especially by a system equipped with an X-ray tube having sufficient power to enable high image quality and 3D reconstruction, and secondly to meet the needs of operating, rooms especially through a system that is capable of moving the X-ray machine

BRIEF SUMMARY OF THE INVENTION

According to an embodiment of the present invention, a mobile base on which is mounted an X-ray machine comprising an X-ray tube configured to emit an X-ray beam along a direction of emission, and an X-ray detector aligned in the direction of emission of the X-ray beam and positioned to face the X-ray tube, is provided. The mobile base comprises: two orientable drive wheels driven respectably by a traction motor and a direction motor; a processing unit coupled to the traction motor and the direction motor, wherein the processing unit is configured to input an instruction value on destination, an instructed value on trajectory and data on position of the X-ray machine, and to generate as an output a respective direction and speed for each drive wheel; and at least one sensor configured to provide the data on position of the X-ray machine.

According to another embodiment of the present invention, an X-ray machine is provided. The X-ray machine comprises: an X-ray tube configured to emit an X-ray beam along a direction of emission; an X-ray detector aligned in the direction of emission of the X-ray beam and positioned to face the X-ray tube, wherein the X-ray machine is mounted on a mobile base comprising: two orientable drive wheels driven respectably by a traction motor and as direction motor; a processing unit couple to the traction motor and the direction motor, wherein the processing unit is configured to input an instruction value on destination, an instructed value on trajectory and data on position of the X-ray machine, and to generate as an output a respective direction and speed for each drive wheel; and at least one sensor configured to provide the data on position of the X-ray machine.

BRIEF DESCRIPTION OF THE DRAWINGS

The invention will be understood more clearly from the following description and from the accompanying figures. These figures are given purely by way of an indication and in no way restrict the scope of the invention.

DETAILED DESCRIPTION OF THE INVENTION

Figure 1:
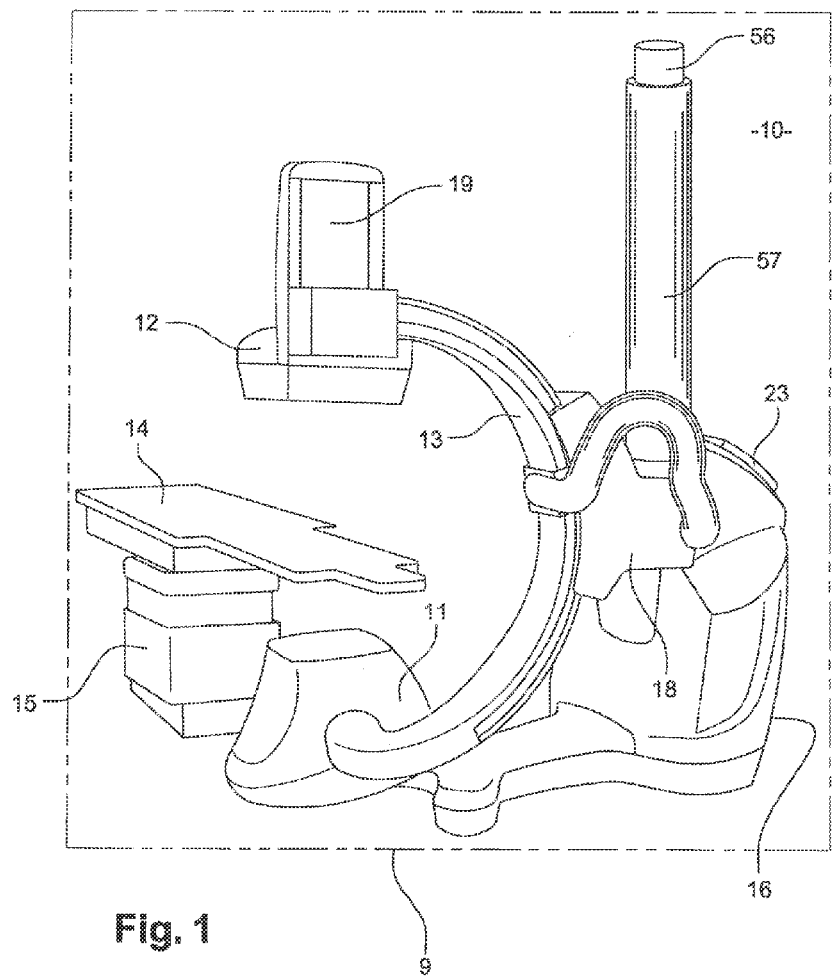
FIGS. 1 and 2 are a schematic representation of a vascular type X-ray machine mounted on a mobile base, according to an embodiment of the invention.

FIG. 1 shows a vascular type X-ray machine 10 in an examination room or surgical ward or hybrid room represented in the form of a frame referenced 9. The X-ray machine 10 has moving parts that can rotate in different directions around a patient. These moving parts are capable of moving in all three dimensions of a space. These moving parts are formed in general by an arm 13 comprising an X-ray tube 11, which is the X-ray source, at one of its ends and a detector 12 at another of its ends. This tube 11 is used to send an X-ray beam along a direction of emission. In general, the arm 13 is C-shaped.

The detector 12 is hooked to the arm 13 opposite the tube 11 and in the direction of emission. The X-ray tube 11 and the image detector 12 are mounted at the opposite ends of the arm 13 so that the X-rays emitted by the tube 11 are incidental to and detected by the image detector 12. The detector 12 is connected to a lift 19 used to raise and lower said detector in the direction of emission.

The room 9 also has an examination table 14, or a bed, on which a patient reclines. The examination table 14 can be mounted on a frame 15 fixed to the ground. The examination table 15 can also be an operation table with a moveable frame.

During a radiography examination, the X-ray machine 10 is shifted in position in working mode so that the organ to be examined is positioned in the X-ray beam.

The arm 13 is mounted on a mobile base 16 through a support element 17. The support element 17 is mounted fixedly on the mobile base 16. The arm 13 is connected to the support element 17 by means of a rotating arm 18. The arm 13 is mounted so as to be sliding relative to the rotating arm 18. & The rotating arm 18 rotates about an axis passing through the X-ray beam. This rotating assembly of the arm 18 on the element 17 enables the X-ray tube 11 and the image detector 12 to be shifted rotationally around the arc of the rotating arm 18. The support element 17, the rotating arm 18 and the arm 13 are thus all three hinged relative to one another. This hinging enables the X-ray machine 10 to move in three dimensions. This movement in three dimensions of the moving parts of the X-ray machine 10 is used to achieve images of the organ to be examined at different values of incidence.

By combining the rotational motions of the moving parts of the X-ray machine 10, the X-ray beam can describe all the directions of emission of the X-rays included within a sphere whose center corresponds approximately to an isocenter 69 of the X-ray machine 10 with a diameter substantially equal to the distance between the tube 11 and the detector 12. The isocenter 69 is situated in a space included between the X-ray emission tube 11 and the X-ray reception detector 12. The isocenter 69 corresponds to the center of the arc of a circle made by the arm 13. The mobile base 16 is designed to move the X-ray machine 10 on the ground. The mobile base 16 is controlled automatically by a processing unit 50. This processing unit 50 can be embedded in the mobile base or kept at a distance in a control room which can be situated outside the examination room 9. In the latter case, the mobile base 16 can be controlled through a radiofrequency or wire type connection using any type of communications protocol.

Figure 2:
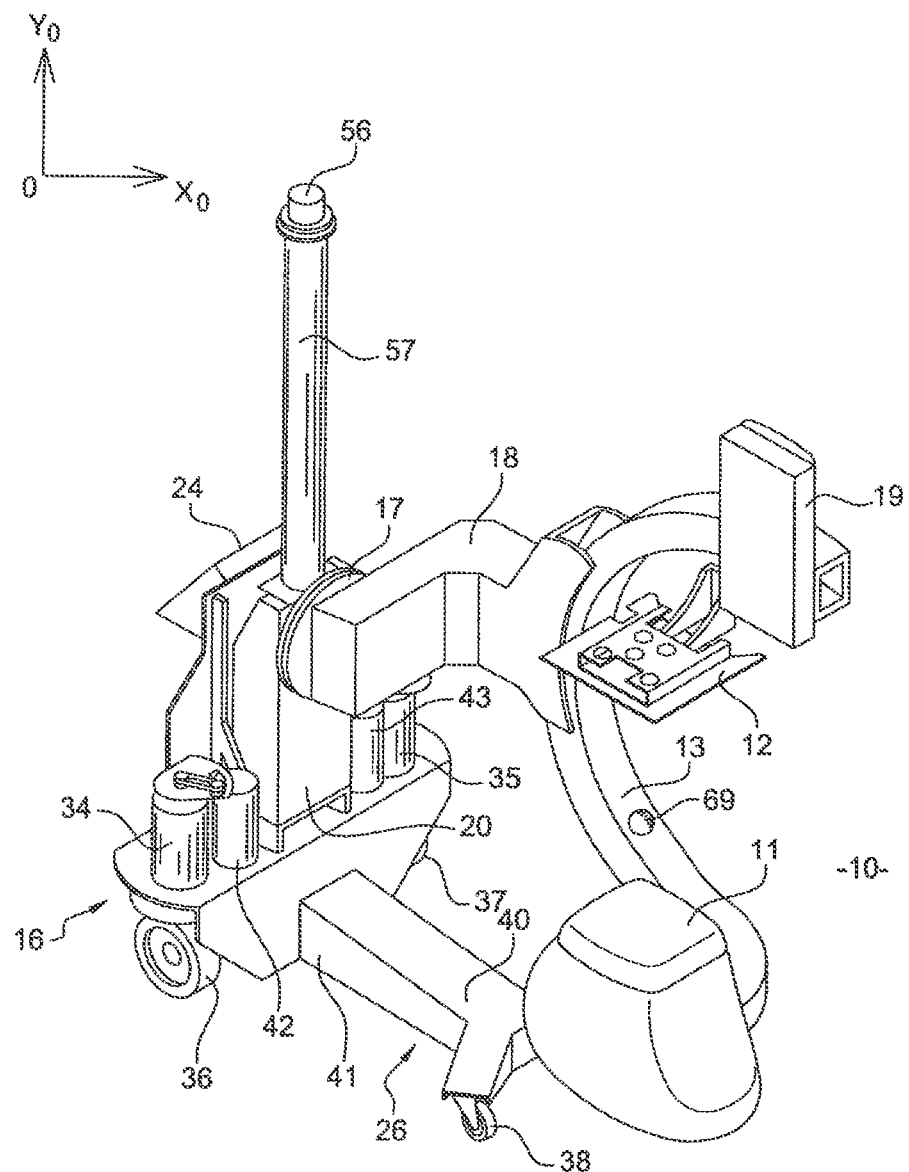
Figure 3:
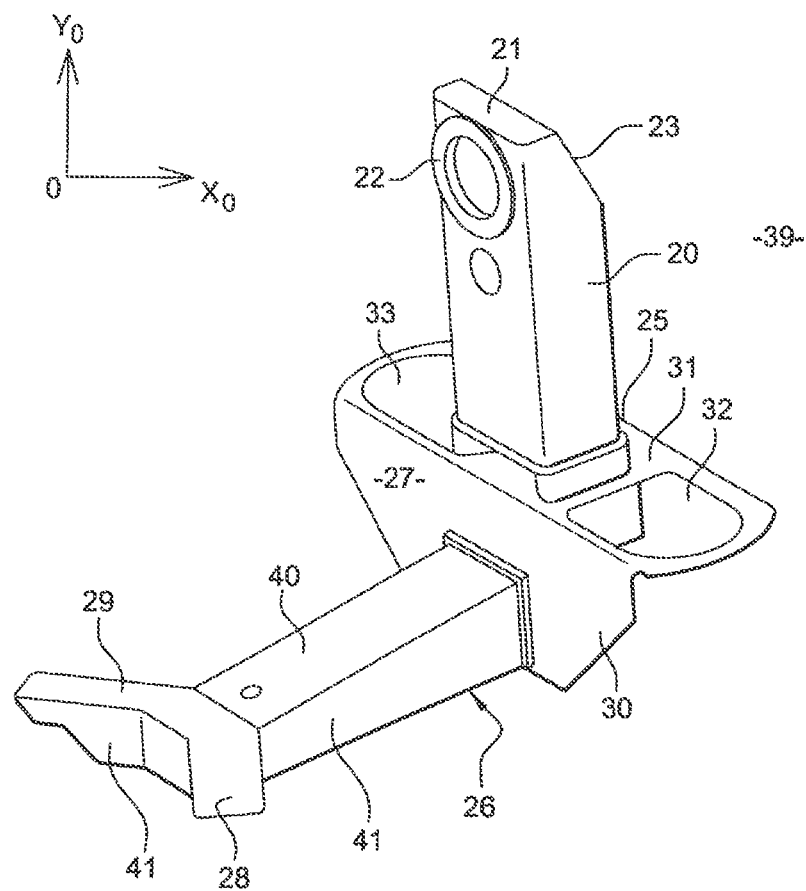
FIG. 3 is a schematic view of a support structure of a mobile base on which the X-ray machine is mounted, according to an embodiment of the invention.

FIG. 2 provides a detailed view of the characteristics of the mobile base 16. As illustrated in FIG. 3, the mobile base 16 has a support structure 39. This structure may comprise several parts joined by screwing or by soldering. This structure 39 may also be a cast element. This support structure 39 has a set of structural pans whose joining and geometrical configuration are designed so that: a suitable support on the ground is provided for the mobile base 16 by a deformation of the set of structural parts forming the support structure 39, and the mobile base 16 is given the rigidity that is necessary and sufficient to eliminate the problem of hyperstatism which may be caused by the four wheels of the mobile base 16 laid on the ground. The structural support 30 ensures that all four wheels of the mobile base 16 will be permanently in contact with the ground, supporting the apparatuses of the mobile base 16 which may be especially motors, wheels, a man-machine interface etc. The layout of these apparatuses in the support structure 39 is also designed so that the weight of the support structure 39 and of the apparatuses balances the weight of the X-ray machine 10.

The purpose of this balancing is to ensure the stability of the X-ray machine X-rays, even during a shift of the moving parts of said machine. The mobile base 16 thus has the role of a counterweight which means that is can maintain the static and dynamic stability of the X-ray machine 10, the apparatuses and the support structure 39. In one example, the weight of the base mobile may be in the range of 500 kg relative to the weight of the X-ray machine 10 which may be in the range of 300 kg.

The support structure 39 has a supporting area 20 extending along the longitudinal direction Yo of a Cartesian reference system Ro. The supporting arm 20 has, for example, a substantially tubular shape. In one embodiment, the supporting arm 20 is one meter high and has a rectangular section of 30 cm by 20 cm.

At one upper end 21, the supporting arm 20 has joining means 22, geometrically and structurally designed so as to receive the support element 17. In the example illustrated by the figures, the joining means 22 and the support element 17 are circular. The joining, means 22 may be fixed to the support element 17, for example by a screw/nut system or by soldering.

Figure 6:
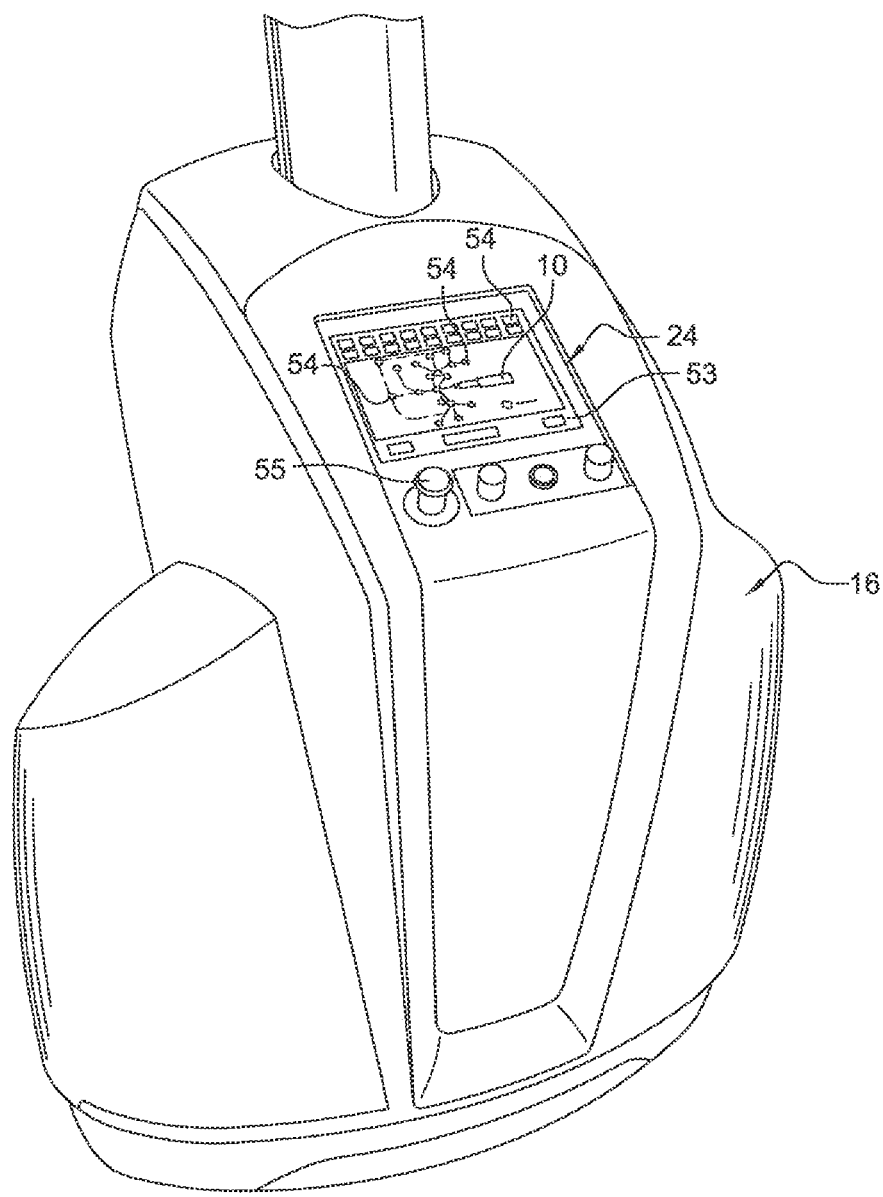
FIG. 6 is a schematic view of a man-machine interface of the X-ray machine used to enter instructed values of destination for said apparatus, according to an embodiment of the invention.

In a preferred embodiment, the mobile base 16 has a receiving means on a face 23 opposite the joining means 22. On these receiving means, it is possible to mount a man/machine interface 24. FIG. 6 shows an example of a man/machine interface 24.

The support structure 39 has a set 26 of rigid metal structures resting on the ground by means of wheels 36, 37 and 38. This set 26 is joined with the supporting arm 20. A front part of the set 26 is substantially V-shaped in the horizontal position. The set 26 has a baseplate 27 situated on a rear part of the Y-shape fixedly joined to a crossbar 40. This baseplate 27 is the structural part connecting the set 26 to the supporting arm 20.

The bar 40 is fixedly joined to an element formed by two arms 28 and 29 having a corner. The fixed joining can be obtained by soldering or any other type of fastening system. For reasons of resistance to stresses, it is generally necessary to line the edges of the arms 28 and 29 and the edges of the crossbar 40 with a vertical reinforcement part 41 which is a rigid lateral metal strip.

Figure 4:
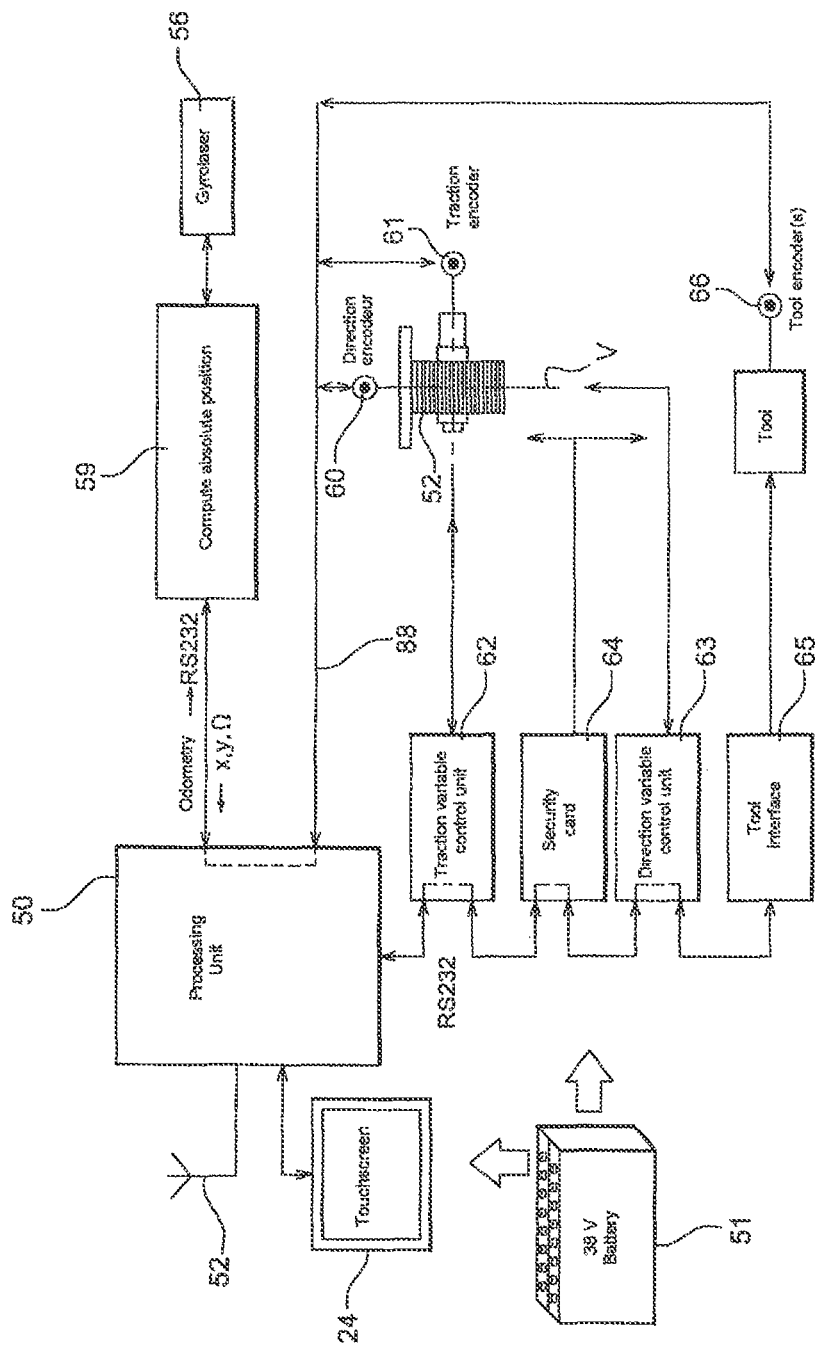
FIG. 4 is a schematic illustration of modules for implementing the operation of the X-ray machine controlled by a processing unit, according to an embodiment of the invention.

The baseplate 27 has a vertical frame 30 supporting a horizontal plate 31 equipped with two turret features 52 shown in FIG. 4. A lower end 25 of the supporting arm 20 is fixed to the frame 30. This fastening can be obtained by soldering or any other type of fastening system.

The choice of the materials, the dimensions, the shape and the thicknesses of the parts of the unit 26, the vertical reinforcement pieces 41 as well as the layout of these parts and reinforcement pieces within the internal structure provides mechanical characteristics of rigidity to the unit 26 relative to the supporting arm 20. These mechanical characteristics of rigidity are designed to compensate for changes in shape due to the weight of the machine 10 supported by the mobile base 16 and to absorb vibrations and secondarily the noise of the X-ray machine 10. These mechanical characteristics enable the formation of points of stabilization of the X-ray machine 10 at the ends of the arms 28 and 29 and the baseplate 27.

In one example, the angle formed by the two arms 28 and 29 may be of the order of 90 degrees and the height of the vertical reinforcement parts 41 may be of the order of 20 centimeters.

In one embodiment, the flexible and noise-free material may furthermore be inserted at the point where the crossbar 40 is fixedly joined to the frame 30 of the baseplate 27. This addition of flexible material is designed to reinforce the deformation of the support structure 39 providing for a balanced support to the four wheels on the ground. This addition of flexible material also improves the mechanical characteristics of rigidity of the set 26 relative to the supporting arm 20. In one embodiment, the flexible material is rubber. In one embodiment, the supporting arm 20 and the Y-shaped unit 26 are made of steel.

Each of the two turret features 52 rotates about a vertical axis V. Each turret is equipped respectively with a traction motor 34 and 35 and a direction motor 42 and 43. A wheel 36 is driven by the two motors, namely the traction motor 34 and the direction motor 42. A wheel 37 is driven by the two motors, namely the traction motor 35 and the direction motor 43. The direction motors 42 and 43 respectively provide for rotation of the wheel 36 and 37 on the vertical axis.

The mobile base 16 supports the two driving motor turret features 52. The two turret features 52 are fixed to the horizontal plate 31. To this end, the horizontal plate 31 has two holes 32 and 33 configured so as to respectively receive one of the two turret features 52. Each of the two turret features 52 can be controlled independently of the other.

The wheel 36 rotates at the speed A and is oriented at an angle $\alpha$ and a wheel 37 rotates at the speed B and is oriented at an angle $\beta$. The speeds A and B are often different and the angles $\alpha$ and $\beta$ are often different. These different speeds and angles of the two drive wheels 36 and 37 enable the X-ray machine 10 to be moved in an examination room 9, in minimizing the volume traversed by said apparatus to the maximum extent. Indeed, the rotational center of the machine 10 can be placed anywhere by means of the different speeds and angles of the two wheels 36 and 37. This independence also enables the machine 10 to move parallel to the set 26. In general, the different speeds and angles of the two wheels 36 and 37 provide for all possible movements in an examination room 9.

The mobile base 16 furthermore has a freewheel system. This system has two free wheels 38 respectively mounted on a face before the ground of one of each arm 28 and 29 of the counterweight system 26. These two freewheels 38 mounted rotationally are capable of undergoing rotational movements induced by the drive wheels 36 and 37.

The mobile base 16 thus has four multidirectional wheels so as to be able to move the machine 10 in every direction. These wheels are placed, symmetrically in sets of two, with the freewheel system which constitutes the from train and the driving and directional wheels 36 and 37 which constitute the rear train. In one alternative embodiment, the wheels may be placed asymmetrically.

Figure 9:
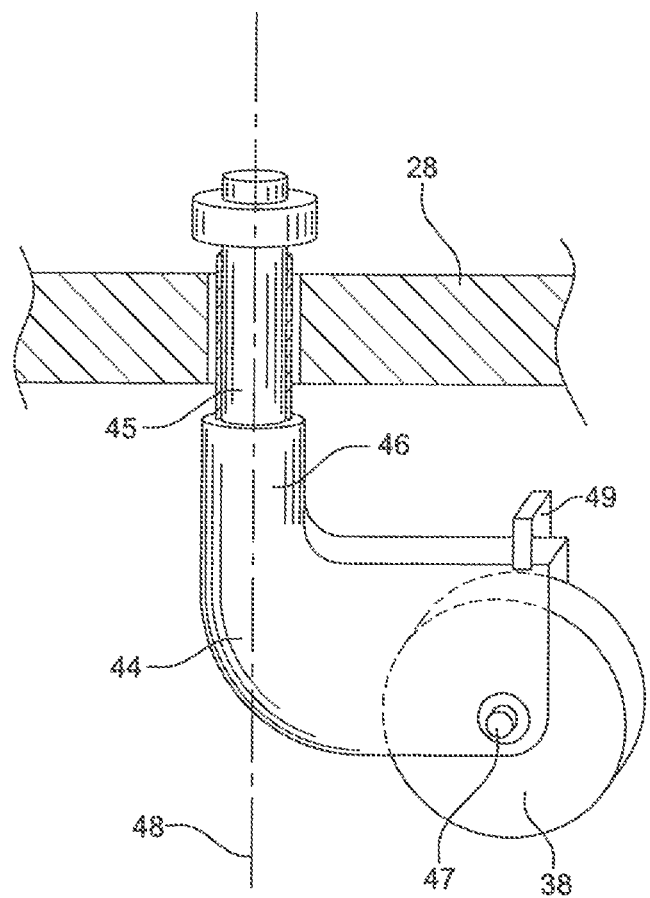
FIG. 9 is a perspective view of the freewheel system according to an embodiment of the invention.

FIG. 9 shows a large-scale view in perspective of an example of a freewheel 38 mourned on the arm 28. It is known that this assembly is identical for the arm 29.

A cover 44 is designed to receive a rotation pin 47 of the wheel 38. An upper part 46 of the cover 44 is mounted, beneath the arm 28, so as to pivot about a vertical rotation axis 48. This pivoting assembly can be obtained by means of a screw/nut fastening system providing for one degree of freedom in rotation. A spacer 45 may go through a space made in the arm 28 to block the nut while at the same time enabling the rotation of the rotational axis 48.

The vertical rotation axis 48 of the freewheel 38 is fixed so as to have an axis that is offset relative to the supporting base of the freewheel 38 on the ground. When the mobile base 16 is shifted in a determined direction, each free wheel gets oriented by rotation about the vertical rotation axis 48 so as to prevent the freewheel 38 from getting jammed.

The freewheel system may furthermore include a braking device designed to block the rotation of the freewheels 38 firstly about the vertical rotation axis 48 and secondly about the rotation shaft 47. In the example of FIG. 9, the cover 44 has a braking device 49 comprising a blocking unit which is herein fixed to the peak of its lower part. This breaking device 49 can be controlled manually or remotely for example by means of the control unit 50. The braking device 49 is configured so that its actuation causes the rotation of the wheels 38 to stop and immobilizes it by blocking the rotation of the axis 48 and the shaft 47.

Thus, when the machine 10 is in the working position and at a stop, the fact that the freewheels 38 are immobilized prevents them from moving during the phases of acceleration and deceleration of the moving parts of the machine 10.

The braking device 49 can be mounted in the rotation shaft 47 of the wheel 38 or at the spacer 45 and in the rotation axis 48. It can be made by any type of existing braking device whose function is to stop the wheel 38 and to keep it stopped.

With the invention, it is thus possible to easily change the region of interest to be examined by: shifting the mobile base 16 from one working position to another by means of the driving and steerable wheels 36 and 37, and moving the moving parts to another given orientation while at the same time keeping the organ to be examined under the X-ray beam.

It must be noted that the element with the arms 28 and 29 is positioned at a sufficient distance from the X-ray tube so that its front end, supporting the freewheels 38, do not come into collision with the hood of the tube 11 in any of the positions that it may take. This configuration makes it possible to increase the distance between the tube 11 and the isocenter 69 of the X-ray machine 10. Through the shifting of the arm 13 along the arc, the tube 11 and the detector 12 can rotate about the isocenter 69 while at the same time keeping their face-to-face relationship. The tube 11 and the detector 12 are positioned on either side of the patient, generally one of these elements being on top of the patient and the other beneath the table 14 which is transparent to X-rays. An increase in the distance between the tube 11 and the isocenter 69 releases the space situated beneath the table 14 relative to the isocenter in order to enable not only the placing of one of these elements but also its movement according to different, at times complex, angulations.

This increase in distance between the tube 11 and the isocenter 69 makes it possible to obtain an X-ray machine 10 capable of carrying out complex angulations and 3D reconstructions of organs situated at the periphery of the body, for example the patient's liver. According to this embodiment of the invention, the distance between the tube 11 and the isocenter 69 may be increased by about 10% as compared with an existing X-ray machine that is fixed to the ground and has the same mechanical geometry.

FIG. 4 is a block diagram of the working of the mobile base 16 controlled by the processing unit 50. In the example of FIG. 4, only one of the turret features 52 is represented, it being understood that the second turret feature which is not represented works identically. In this example, the turret feature 52 that is shown comprises the traction motor 34 and the direction motor 32 which are designed to drive the wheel 36.

Figure 5:
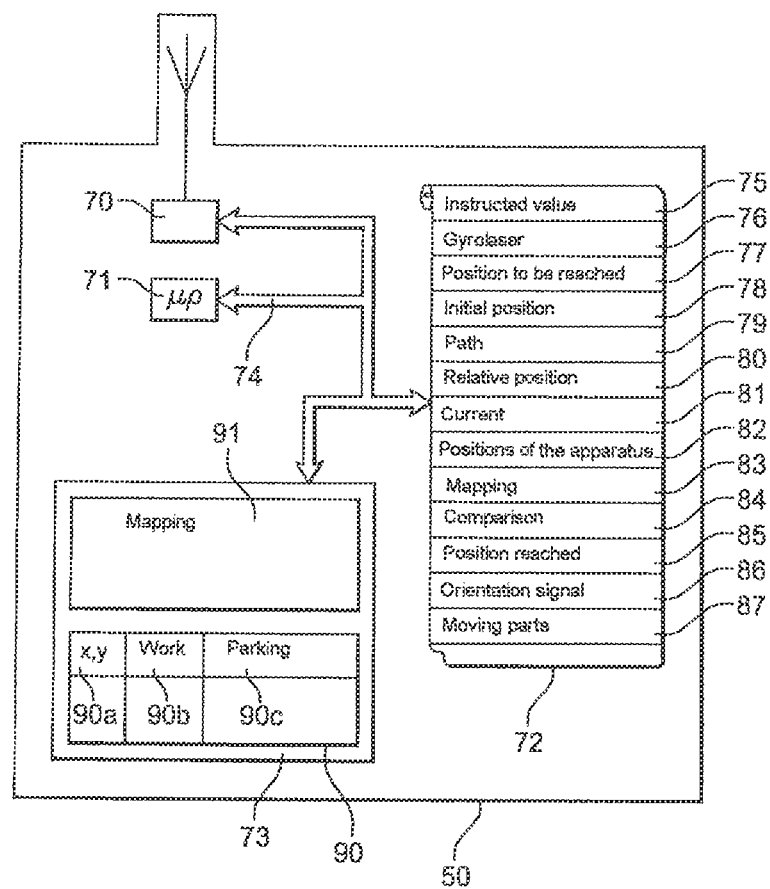
FIG. 5 is a schematic and detailed view of the processing unit of FIG. 4.

The processing unit 50 is represented in detail in FIG. 5. The processing unit 50 is connected to the DC or rectified power source 51. This source 51 may also be a rechargeable battery.

The processing unit 50 communicates especially with the interface 24 and/or supervision computer which sends it especially the instructed values on destination.

In one embodiment, the processing unit 50 and the interface 24 are connected through a communications bus 88.

In one alternative embodiment, the interface 24 may be set away from the mobile base 16. In this case, it may be placed on the examination table 14. The communications between the processing unit and the interface 24 set at a distance may be obtained by means of a wireless link. The wireless link may be of any type without departing from the framework of the invention. For example it may be an infrared, ultrasonic, or radiofrequency link, based for example on an industrial standard such as the ZigBee standard or a proprietary standard or again it may be obtained in a frequency band associated with a given protocol such as Wi-Fi Bluetooth etc. To this end, the processing unit 50 has an antenna 52 which enables it to obtain a radio electrical link with the interface 24 set at a distance.

Communications between the interface 24 set at a distance and the processing unit 50 can also be obtained through a wire link.

A representation of the man-machine interface 24 is illustrated in FIG. 6. FIG. 6 shows a top view of the mobile base 16. The man-machine interface 24 herein is a touchscreen 53. In on variant, this interface 24 may be a screen associated with a keyboard. The interface 24 may be powered by the source 51. In one variant, it may be powered by a distinct energy source.

This touchscreen 53 has interface controls 54 displayed on the screen. These interface controls 54 correspond to predefined working and parking positions of the X-ray machine 10 in the room 9. The controls 54 may be displayed on the screen 53 by letters, figures or by a graphic representation. This interface 24 is aimed at making it easy for an operator to enter an instructed value of destination by pressing one of the interface controls 54 displayed on the screen 53. This interface 54 is complemented by a set of control buttons such as emergency stop buttons 55 or buttons for starting the mobile base 16.

The processing unit 50 is coupled to an optical position sensor 56. The optical position sensor 56 is mounted on an upper end of a connection pole 57. A lower end of the connection pole 57 is fixed to the supporting arm 20 of the mobile base 16. In one variant, the connection pole 57 may be fixed to the horizontal plate 31 in the vicinity of the supporting arm 20. This type of mounting of the pole 57 removes the need to transmit the vibrations of the supporting arm 20 to the sensor 56.

The optical sensor 56 is used to measure an angle or an angular speed about at least one axis. It can also be used for the precision measurement of the position of the X-ray machine 10 relative to a predefined fixed reference system Ro (Xo, Yo).

The optical sensor 56 shown in FIG. 2 has a general optical constitution that is known and will therefore be described only very briefly. The optical sensor 56, here below called gyrolaser, generally has inter alia a laser emitter device and a system for the rotation of the emitter device. The emitter device emits a pulsed incident laser beam 68.

Figure 7:
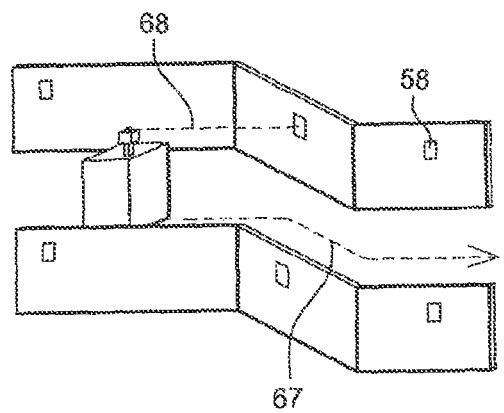
FIG. 7 is a schematic view of the X-ray machine moved by means of the mobile base in a room along a predefined path, according to an embodiment of the invention.

As can be seen in FIG. 7, the room 9 is preliminarily provided with laser beam reflectors 58 placed at predetermined positions. These reflectors 58 may be catadioptric reflectors. The reflectors 58 are placed on the demarcating walls of the room 9 at a height such that they can detect the incident laser beam 68.

The positioning distance between two successive reflectors 58 is determined so as to increase the precision of the gyrolaser 56. In one example, the reflectors 58 may be at a height of about 2.5 m from the ground and the minimum distance between two reflectors may be in the range of 2 m. In a room 9 having surface area of about 60 m$^2$, the number of reflectors 58 may be of the order of 10.

When the incident laser beam 68 encounters a reflector 58, this reflector 58 reflects towards the gyrolaser 56 which has a system for reading reflected laser beams.

The reading system 59 has means to measure the time taken by the incident beam to return to the gyrolaser 56. These measuring means are capable of determining a distance with precision on the basis of the time measured. The measuring means associate the determined distance with an angular position by means of an optical encoder which is precise to a tenth of a degree. To this end, a card comprising positions (coordinates in the fixed reference system) of the set of reflectors 58 is recorded beforehand in a data memory (not shown) of the reading system 59. Depending on the position of the reflectors 58 that have emitted the reflections received and on the angular speed, the reading system 59 computes the angle Ω of orientation of the machine 10.

The reading system 59 also has computation means capable of determining an absolute position of the gyrolaser 56 corresponding to that of the X-ray machine 10 as a function of the reflections received in one turn of the emission device and of the chart of positions of the reflectors 58 recorded in the data memory.

The reading system 59 may be a computer. The actions performed by this reading system 59 are arranged in order by a microprocessor (not shown). The microprocessor, in response to the instruction codes recorded in a memory, produces the angle α and the coordinates of the X-ray machine in the fixed referential system.

Figure 8:
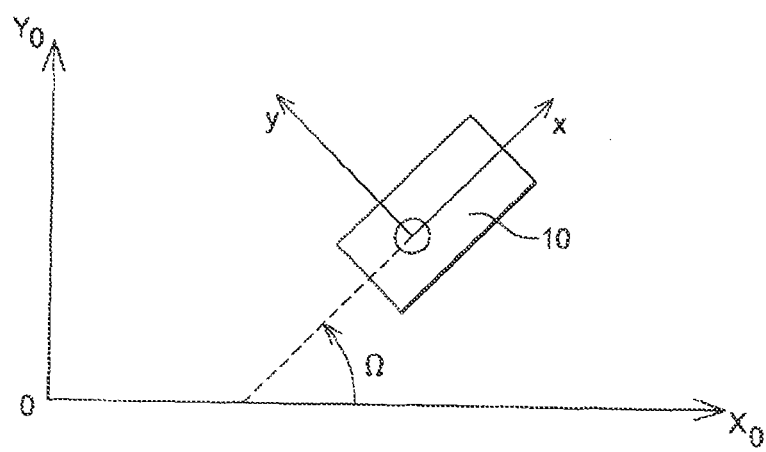
FIG. 8 is a graphic representation of an absolute position of the mobile base in a fixed Cartesian reference system, according to an embodiment of the invention.

FIG. 8 is a graphic representation of the X-ray machine 10 in a Cartesian reference system. The orientation of the machine 10 is identified by the angle Ω which corresponds to the orientation of a local reference system R (x, y) in the fixed reference system Ro (Xo, Yo). The fixed reference system Ro corresponds to an initial reference in an idle phase of the machine 10 in the local reference system. The angle Ω and the coordinates of the machine 10 in the local reference system R(x,y) are given by the gyrolaser 56.

The fixed reference system Ro is characterized by a set of unit vectors (i, j), respectively representing, the direction of the axes OXo, OYo. In one embodiment, the fixed reference system Ro is a Cartesian reference system joined to the examination table 14, when this table is fixed to the ground through the frame 15. In this case, the x-axis OXo of the fixed reference system corresponds to the horizontal plane of the examination table 14. In one variant, the fixed reference system Ro may be any unspecified, predefined Cartesian reference system in the room 9.

The reading system 59 is coupled to the processing unit 50 by the communications bus 88 and transmits information elements to it on the angle Ω and on the coordinates of the machine 10 relative to the local reference system. These information elements constitute the absolute position of the machine 10.

The processing unit 50 drives the traction motor 34 and the direction motor 42, proper to the wheels 36, in managing the supply of energy as a function of the absolute position of the machine 10 and the path 67 to be followed.

Since, during one full rotation of the gyrolaser 56, the mobile base 16 will have moved, the measurement of absolute position should be supplemented by other measurements to improve its position.

To obtain these supplementary measurements, an angular position sensor 60 is planned on the direction motor 42. This angular sensor 60 is used to find out the orientation of the driving and directional wheel 36 at each instant. The angular position sensor 60 can be of many types, for example an optical sensor, a resolver type or synchro type rotary transformer sensor etc.

Furthermore, the traction motor 34 is also provided with a wheel speed sensor 61. The information coming from the signals of the set of sensors 60 and 61 constitute the relative position of the machine 10. This relative position of the machine 10 enables the processing unit 50 to update the absolute position should there be a decline in the precision of the laser measurement.

At each point in time, the processing unit 50 makes a relatively precise estimation of the speed of each wheel relative to the ground, by combining data on the relative position of the machine 10 with data on absolute position.

The traction motor 34 is controlled by a traction variator 62. The direction motor 42 is controlled by a direction variator 63. This traction variator 62 and direction variator 63 are connected to the processing unit 50 through the communications bus 88. The variators 62 and 63 respectively receive instructed values of speed and direction from the processing unit 50 which they convert into current and into voltage for each motor.

The traction variator 63 and the direction variator 63 are used to generate an electrical differential as a function of the instructions sent out by the processing unit.

These differentials are designed to share the propulsion force and the rotational angles between the two wheels 36 and 37 so that they can travel along the programmed path 67. The processing unit 50, using the variators, dictates the currents in the traction and direction motors as a function of information representing especially the speed and angular direction of the driving wheels 36 and 37 as measured, and instructed values on the positioning of the operator, the absolute position of the X-ray machine 10 and the path 67 to be followed.

The machine 10 is furthermore provided with a safety system 64 coupled by the communications bus 88 with the processing unit. The safety system 64 has a set of sensors (not shown) whose signals transmitted to the processing unit 50 enable this unit to control the emergency stopping system of the mobile base 16 and the moving parts of the machine 10 if necessary.

The sensors may be formed by an inclinometer, an impact sensor and as laser sensor etc. . . .

The processing unit 50 is furthermore coupled with a device 65 for controlling the moving parts of the machine 10. The coupling of the processing unit 50 with the control device 65 can be obtained through the communications bus 88 or through a radio electrical link. This control device 65 may be a joystick or a computer. In one variant, this control device 65 may be incorporated in the interface 24.

The machine 10 is furthermore provided with a sensor 66 for detecting the rotation speed of the moving parts. The sensor 66 is coupled with a processing unit 50 through the communications bus 88. The signals transmitted by this sensor 66 to the processing unit 50 enable this processing unit to control the emergency stopping system of the mobile base 16 and the moving parts of the machine 10 if necessary.

In one embodiment, the activation of the emergency stopping system may be accompanied by a sound and/or optical alarm system.

The communications bus 88 may be an 'RS 232' type series link or an ADC (analogue digital converter) link.

In other words, the automatic driving of the machine 10 is implemented by means of a hardware sequence consisting of positioning sensors such as traction encoders 61 at each traction motor 34 and 35 respectively and direction encoders 60 at each direction motor 42 and 43 respectively, the rotational laser scanning sensor 56, the computer 50, the traction variator 62 and direction variator 63 for each turret feature, the safety sensors and finally the actuators which are the traction motors 34 and 35 and direction motors 42 and 43.

The embodiment of the invention described here above thus implements two distinct navigation systems. One of the navigation systems is obtained from the traction and direction encoders. The other navigation system is obtained from the rotary laser scanning sensor. This redundancy of navigation systems makes it possible not only to specify the absolute position of the X-ray machine but also to improve the safety system of the machine 10. Indeed, when the difference between the position given by the rotary laser sensor and the position given by the encoders is greater than a predefined safety threshold, the processing unit activates the emergency stopping system of the moving parts of the machine 10 and of the mobile base 16.

The processing unit 50 is a computer device, for example a microcomputer programmed to determine the current of the motor according to programmable criteria and to fulfill additional functions pertaining to the management and security of the machine 10.

In the description, when actions are attributed to apparatuses or programs, it means that these actions are executed by a microprocessor of this apparatus or of the apparatus comprising the program, said microprocessor being then controlled by instruction codes recorded in a memory of the apparatus. These instruction codes are used to implement the means of the apparatus and therefore to fulfill the action undertaken.

As illustrated in FIG. 50, the processing unit 50 comprises electronic circuits 70 connected to the antenna 52. The role of the circuits is to provide the radio interface between the processing unit and the external interfaces.

The processing unit furthermore comprises a microprocessor 71, a program memory 72 and a data memory 73 connected to a bidirectional bus 74. The program memory 72 is divided into several zones, each zone corresponding to it function or to a mode of operation of the program of the X-ray machine 10 and of the mobile base 16. Similarly, when an action is attributed to a program, this action corresponds to the implementation by a microprocessor, connected to a memory in which the program is recorded, of all or part of the instruction codes forming said program.

Only the zones of the memory 72 that most directly concern the embodiment of the invention are shown.

A zone 75 comprises instruction codes to receive a movement signal corresponding to the entry of an instructed value of positioning or destination of the X-ray machine 10. The instructed value of positioning may be a parking position or a working position coupled with an orientation of the moving parts of the machine 10.

A zone 76 comprises instruction codes to command the gyrolaser upon reception of the shift signal.

A zone 77 comprises instruction codes to extract the coordinates of the position to be attained by the X-ray machine 10 from the data memory 34, on the basis of the signal received, in the fixed reference system.

A zone 78 comprises instruction codes to interpret the information given by the gyrolaser in order to determine the initial absolute position of the machine 10 in the fixed reference system.

When the initial position determined does not correspond to any ing or working position pre-recorded in the data memory, the instruction codes of the zone 78 compute a path to be taken by the mobile base 16 in order to reach one of positions, namely the parking or the working position, on the basis of data given by the encoders and the gyrolaser. In one embodiment, the processing unit computes the shortest path needed to reach the working or parking position closest to the initial position. A zone 79 comprises instruction codes to extract, from the data memory 34, a path 67 that the machine 10 must take to link the initial position with the position to be reached by the X-ray machine 10.

A zone 80 comprises instruction codes to determine the relative position of the machine 10 as a function of the data given by the sensors installed on the mobile base 16.

A zone 81 comprises instruction codes to give each traction motor 34 and 35 and each direction motor 42 and 43 a current through the power variators as a function of the relative position, the initial position of the machine 10 and the path 67 to be followed.

A zone 82 comprises instruction codes to compute the absolute and relative positions of the machine 10 at predefined computation periods all along the path 67 to be followed. A computation period may be of the order of some milliseconds.

A zone 83 comprises instruction codes to extract a predetermined mapping of the room 9 from the data memory 73.

A zone 84 comprises instruction codes to determine, at each computation period, the position of the machine 10 in the mapping as a function of the data given by the instruction codes of the zone 83. The instruction codes of the zone 84 are superimposed on the path to be followed in the mapping and determine whether the position of the machine 10 is substantially in the path. In the event of deflection, the instruction codes send a compensation command to the variators to command the shifting of the mobile base 16 in the path 67 to be followed.

In this embodiment, the invention thus makes it possible to move the machine 10 along the extracted path 67 which has been pre-computed. The guiding function implemented by the instruction codes of the zone 84 maintain the absolute position on the path in evaluating the differences in position between the measurement coming from the locating operation and the path followed. The positional direction commands that result from this are applied to the variators which themselves set up an automatic feedback control of the motors in position and in speed.

In addition to the guidance, a navigation function can be implemented by the instruction codes of the zone 84 in order to carry out a scheduling of the traction speeds along the path and transmit control commands accordingly to the variators. The variators thus set up an automatic feedback control between the traction and direction motors.

One part of the safety function is implemented at this level by a coupling between direction and traction. In this case, when the deviation of the absolute position measured at the path 67 is greater than or equal to a predefined threshold of deviation, the speed of the mobile base 16 is reduced until it comes to a total halt.

When the machine 10 reaches the position to be reached, a zone 85 comprises instruction codes to deactivate the gyrolaser. These instruction codes also send out control commands to the direction variators so that the wheels are aligned in a predefined idle position.

A zone 86 comprises instruction codes to extract a working orientation signal of the moving parts, corresponding to the reached working position of the X-ray machine, from the positioning instructed value. The instruction codes of the zone 86 are also capable of allowing reception of a work orientation signal for the moving parts of the X-ray machine corresponding to the actuation of the orientation commands of the control device 65.

A zone 87 comprises instruction codes to control a system for driving the moving parts as a function of the orientation signal. This driving system makes it possible to shift the arms 13, the rotating arm 18, the support element 17 and the mobile base 16. The shifting of these parts, which is done as a function of the orientation signal, is done in such a way that the organ to be examined remains positioned throughout the diagnosis in the X-ray beam. In one embodiment, the driving system can be activated during the phases in which the mobile base 16 is being shifted.

The data memory 73 has a data base 90 in which predetermined parking, and working positions of the machine 10 are recorded. These predetermined positions are displayed on the screen by the interface controls. A parking position is a place where the X-ray machine 10 is placed when it is in parking mode. The parking position removes the X-ray machine from the limited space needed for an operation in the room 9. A working, position is a place in which the X-ray machine 10 is placed during the acquisition of radiography exposures.

The data base 90 is, for example, structured in the form of a table. For example, each row of the table corresponds to the coordinates of a position of an X-ray machine in the fixed reference system, each column of the table corresponding to a piece of information on this position. Thus, the database 90 comprises: a row 90*a* corresponding to the coordinates of a position in the fixed reference system, a column 90*b* comprising a first field in which a signal of a working position is recorded, a second field in which an orientation signal corresponding predetermined working orientations of the moving, parts of the X-ray machine 10 are recorded and a third field in which a path to be followed is recorded, and a column 90*c* comprising a first field in which a parking signal is recorded, and a second field in which a path to be followed is recorded.

A working orientation is a configuration of the X-ray machine in which the arm 13, the rotating arm 14, the support element 17 and the mobile base 16 are shifted to a radiography position according to the orientation signal. This shift does not affect the position of the organ to be examined relative to the X-ray beam.

The data memory 73 also has a data base 91 in which a mapping of the room 9 is recorded.

The data/memory bases have been represented only by way of an illustration of the layout of components and data recordings. In practice, these memories are unified and distributed according to constraints of size of the data base and/or the speed of the processing operations desired.

The invention is not limited to the embodiments described, here above. Indeed, in one embodiment, the man-machine interface 24 may be supplemented or replaced by a joystick-type control lever with three degrees of freedom, along two orthogonal directions and one rotation at an angle θ. The joystick can be mounted on the mobile base 16 or set off at a distance.

The communication between the joystick and the processing unit 50 can be done through a radioelectrical link or a wire link such as a series link, depending on the embodiments of the invention. The joystick sends the processing unit 50 control signals for the variators.

The joystick may comprise a base unit and a unit forming a movable handle that can be tilted in every direction and can be manipulated along several degrees of freedom. Under the effect of the movement of the unit forming a handle relative to the base unit, the processing unit sends the traction variator 62 and direction variator 63 respectively instructed values of speed and direction which they convert into current and voltage for each motor. A movement of the handle-forming unit relative to the base unit in one direction activates a command for moving the mobile base 16 in one direction or another depending on the direction of shift programmed in the processing unit 50.

The joystick is thus capable of controlling the movements of the mobile base 16 in the room 9 according to signals received by the processing unit 50.

The data provided by the gyrolaser to the processing unit 50 can be used to find out the geographical position of the machine 10 in the room 9 in real time in order to prevent possible collisions for example with the examination table 14.

In one alternative embodiment, the interface 24 may be supplemented or replaced by a remote control wireless type control lever capable of steering the movement of the mobile base 16 in two orthogonal directions and a rotation by an angle θ.

What is claimed is:

1. A mobile base configured to support a medical imaging machine comprising:
    at least one motorized drive wheel;
    an optical positioning system comprising a gyrolaser, a reading system and a memory, the system configured to compute position data corresponding to a position of the medical imaging machine in a predefined fixed referential system on the basis of reflections from reflectors positioned about a defined space, the positions of the reflectors stored in the memory; and a processing unit in communication with the at least one motorized drive wheel and the optical positioning system, and configured to receive the position data corresponding to the position of the medical imaging machine and generate a corresponding output for controlling direction and speed of the at least one motorized drive wheel to move and orient the mobile base to one or more desired positions in the defined space.

2. The mobile base of claim 1, wherein the medical imaging system is an X-ray machine.

3. The mobile base of claim 1, wherein the reflectors are catadioptric reflectors.

4. The mobile base of claim 1, further comprising a traction encoder mounted on the at least one motorized drive wheel, wherein the traction encoder and a direction encoder are configured to provide data relative to a position of the X-ray machine.

5. The mobile base of claim 2, further comprising a support structure comprising:
   a supporting arm comprising an upper end to which the X-ray machine is designed to be fixed; and
   a set of structural parts resting on the floor comprising at least one wheel and being assembled with the supporting arm,
   wherein the supporting arm and the set of structural parts are configured to give the mobile base mechanical characteristics of rigidity relative to the supporting arm.

6. The mobile base of claim 5, wherein the set of structural parts comprises:
   a baseplate fixed to the supporting arm, the baseplate comprising a horizontal plate on which the at least one motorized drive wheel is installed;
   a crossbar fixedly joined to the baseplate; and
   an element with two arms having an angle and being fixedly joined to the crossbar, the arms being situated on a front part of the X-ray machine.

7. The mobile base of claim 6, wherein the element with two arms is positioned at a determined distance so that the front ends of the arms do not collide with an X-ray tube, and the distance between the tube and an isocenter of the X-ray machine is maximized.

8. The mobile base of claim 6, wherein the edges of the arms and of the crossbar are lined with vertical reinforcement parts.

9. The mobile base of claim 6, wherein a plastic flexible material is inserted at the position where the crossbar and the baseplate are fixedly joined.

10. The mobile base of claim 6, further comprising at least one freewheel mounted on one end of each arm on a face before the ground, wherein the at least one freewheel is mounted so that a rotational axis of the at least one freewheel is off-center relative to a supporting base of the at least one freewheel on the ground.

11. The mobile base of claim 10, further comprising a braking apparatus mounted on the at least one freewheel, wherein the braking apparatus is configured to block the rotation of the at least one freewheel and keep the at least one freewheel stopped.

12. The mobile base of claim 6, further comprising a connection pole having a lower end and an upper end, wherein the lower end is fixed to the support structure and the upper end bears a gyrolaser.

13. The mobile base of claim 1, further comprising a man-machine interface in communication with the processing unit for entering at least one of instructed values of destination and instructed values of trajectory.

14. The mobile base of claim 13, wherein the man-machine interface is embedded in the mobile base or placed at a distance from the mobile base.

15. The mobile base of claim 13, wherein the man-machine interface comprises at least one of a touchscreen, a joystick and a remote control unit.

16. The mobile base of claim 1, wherein the mobile base is electrically powered through a battery or a mains supply.

17. The mobile base of claim 1, further comprising a safety system comprising anti-collision and tilt sensors.

18. The mobile base of claim 1, wherein the processing unit is also configured to receive inputs from a user corresponding to at least one of destination, trajectory, and orientation of the mobile base.

19. The mobile base of claim 1, wherein the at least one motorized drive wheel comprises two motorized drive wheels.

20. An X-ray machine comprising:
   an X-ray tube configured to emit an X-ray beam along a direction of emission;
   an X-ray detector aligned in the direction of emission of the X-ray beam and positioned to face the X-ray tube,
   wherein the X-ray machine is mounted on a mobile base comprising:
      at least one motorized drive wheel;
      an optical positioning system comprising a gyrolaser, a reading system and a memory, the system configured to compute position data corresponding to a position of the X-ray machine in a predefined fixed referential system on the basis of reflections from reflectors positioned about a defined space, the positions of the reflectors stored in the memory; and
      a processing unit in communication with the at least one motorized drive wheel and the optical positioning system, and configured to receive the position data corresponding to the position of the X-ray machine and generate a corresponding output for controlling direction and speed of the at least one motorized drive wheel to move and orient the mobile base to one or more desired positions in the defined space.

* * * * *